United States Patent
Piazza et al.

(10) Patent No.: US 11,364,418 B2
(45) Date of Patent: Jun. 21, 2022

(54) DEVICE, SYSTEM AND METHOD FOR AUTOMATED GLOBAL ATHLETIC ASSESSMENT AND / OR HUMAN PERFORMANCE TESTING

(71) Applicants: John Piazza, Staten Island, NY (US); Susan Piazza, Staten Island, NY (US)

(72) Inventors: John Piazza, Staten Island, NY (US); Susan Piazza, Staten Island, NY (US)

( * ) Notice: Subject to any disclaimer, the term of this patent is extended or adjusted under 35 U.S.C. 154(b) by 927 days.

(21) Appl. No.: 16/154,362

(22) Filed: Oct. 8, 2018

(65) Prior Publication Data

US 2020/0108291 A1 Apr. 9, 2020

(51) Int. Cl.
  *A63B 24/00* (2006.01)
  *G06N 20/00* (2019.01)

(52) U.S. Cl.
  CPC ......... *A63B 24/0062* (2013.01); *G06N 20/00* (2019.01); *A63B 2024/0065* (2013.01); *A63B 2024/0071* (2013.01)

(58) Field of Classification Search
  CPC ........ A63B 24/0062; A63B 2024/0065; A63B 2024/0071; G06N 20/00; G16H 50/30; G16H 50/70; G16H 20/30
  See application file for complete search history.

(56) References Cited

U.S. PATENT DOCUMENTS

| | | | |
|---|---|---|---|
| 5,697,791 A | 12/1997 | Nashner et al. | |
| 5,749,372 A | 5/1998 | Allen et al. | |
| 6,032,530 A | 3/2000 | Hock | |
| 6,050,962 A | 4/2000 | Kramer et al. | |
| 6,059,576 A | 5/2000 | Brann | |
| 6,503,173 B2 | 1/2003 | Clem | |

(Continued)

FOREIGN PATENT DOCUMENTS

| | | |
|---|---|---|
| EP | 2263534 A1 | 12/2010 |
| JP | 2011011058 A | 1/2011 |
| WO | WO2014197600 A1 | 12/2014 |

OTHER PUBLICATIONS

Athlete Monitoring Found at: http://www.athletemonitoring.com—date May 25, 2018.

(Continued)

*Primary Examiner* — Dmitry Suhol
*Assistant Examiner* — Alyssa N Brandley
(74) *Attorney, Agent, or Firm* — Ernest D. Buff; Ernest D. Buff & Associates, LLC; Margaret A. Lacroix (57) ABSTRACT

A system, method, and computer-readable media collect and analyze the physical performance of an individual and structure and generate an athletic protocol. Athletic assessment devices perform an athletic assessment of an individual, including kinetic, neurological, musculoskeletal and aerobic capacity. Athletic data is collected and stored in a digital data storage medium of a computer system having a display, and a central processing unit (CPU) operable with programming executes one or more analytical algorithms to assess injury risk levels of said individual based on said athletic data. Data mining algorithms using artificial intelligence are used to execute predictive modeling and analytics. The resultant athletic protocol includes information to correct imbalances to treat and/or prevent injuries, corrective exercises, performance training exercises, and protocols to maximize physical performance.

19 Claims, 4 Drawing Sheets

(56) References Cited

U.S. PATENT DOCUMENTS

| | | | |
|---|---|---|---|
| 6,626,800 | B1 | 9/2003 | Casler |
| 7,074,168 | B1 | 7/2006 | Farnes et al. |
| 7,264,554 | B2 | 9/2007 | Bentley |
| 7,278,966 | B2 | 10/2007 | Hjeit et al. |
| 8,287,435 | B2 | 10/2012 | Chape, Jr. et al. |
| 8,292,788 | B2 | 10/2012 | Chape, Jr. et al. |
| 2005/0014113 | A1 | 1/2005 | Fleck et al. |
| 2013/0244211 | A1* | 9/2013 | Dowling ............... G16H 20/30 |
| | | | 434/247 |
| 2016/0220864 | A1 | 1/2016 | Hollins et al. |
| 2016/0027325 | A1 | 8/2016 | Malhotra |
| 2017/0169718 | A1 | 6/2017 | Smith |
| 2017/0266498 | A1 | 9/2017 | Sanders et al. |
| 2019/0366154 | A1* | 12/2019 | Callaghan .......... A63B 21/0724 |
| 2021/0145367 | A1* | 5/2021 | Wagner ............... A61B 5/1036 |

OTHER PUBLICATIONS

Kitman Labs Found at: http://www.Kitmanlabs.com—date May 25, 2018.

* cited by examiner

DEVICE, SYSTEM AND METHOD FOR AUTOMATED GLOBAL ATHLETIC ASSESSMENT AND / OR HUMAN PERFORMANCE TESTING

1. FIELD OF THE INVENTION

The present invention relates to athletic assessment and/or human performance and testing technology used in the fields of physical health and physical/athletic performance that extracts and processes data corresponding to physical or athletic performance and/or human performance for improved health and/or athleticism.

2. BACKGROUND

Research shows that physical/athletic performance or human performance is often limited not by an athlete's or individual's potential, but instead by injuries and suboptimal movement patterns that result from imbalances in biomechanics. Various systems and methods have been implemented to measure and analyze an individual's health and/or athletic/human performance. However, these systems and methods generally fail to collect, analyze and generate an output with precise individualized training that is health-specific, sport-specific and/or position-specific, and ensures optimal performance and/or health of that athlete or individual. In addition, such systems and methods generally fail to provide an output that includes proactive pre-habilitative exercise and recovery methods to improve the range of motion, reduce the risk of injury and maximize performance.

U.S. Pat. No. 5,697,791 to Nashner, et al. discloses devices and methods for the assessment and biofeedback training of coordination skills of a subject critical to maximizing the power and accuracy of athletic ball-strike activities. Embodiments include assessment, biofeedback training and body movement sensor of weight bearing and center of gravity control and under conditions requiring the athlete to strike a ball.

U.S. Pat. No. 5,749,372 to Allen et al. discloses visual and audible outputs indicating a current level of activity to provide immediate and reliable feedback to a user for improved maintenance of at least a desired level of activity.

U.S. Pat. No. 6,032,530 to Hock discloses a method and apparatus for monitoring key components of body movement and flexure during kinetic activities, and providing intuitive, audible, real time biofeedback to the user. The system uses one or more transducers of types that are directionally sensitive to motion, distance, velocity, and the like, or sensitive to flexure of body joints, at frequencies and magnitudes consistent with human physical activities.

U.S. Pat. No. 6,050,962 to Kramer et al. discloses a sensing system provided for measuring various joints of a human body for applications for performance animation, biomechanical studies and general motion capture. One sensing device of the system is a linkage-based sensing structure comprising rigid links interconnected by revolute joints, where each joint angle is measured by a resistive bend sensor or other convenient goniometry.

U.S. Pat. No. 6,059,576 to Brann discloses an electronic device, system and method to monitor and train an individual on proper motion during physical movement. The system employs an electronic device which tracks and monitors an individual's motion through the use of an accelerometer capable of measuring parameters associated with the individual's movement. The device also employs a user-programmable microprocessor which receives, interprets, stores and responds to data relating to parameters.

U.S. Pat. No. 6,503,173 to Clem discloses a personalized training system, and a method of fitness training. The personalized training system includes a fitness device, into which a user enters a first plurality of user information, including a choice of an automated interactive learned program mode or an automated fitness test mode, an automated control location that receives the first plurality of user information, and a second plurality of user information during each use of the fitness device by the user, a performance assessor that assesses a performance of the user during each use of a plurality of uses based on a comparison of the second plurality of user information to the first plurality, a performance database incrementally formed by at least the plurality of performance assessments, and a fitness comparator that adjusts the use based on a comparison of the performance database to the second plurality.

U.S. Pat. No. 6,626,800 to Casler discloses an exercise method that provides a tailor-made exercise protocol that can be modified by a clinician in a supervisory position. A processor with a protocol-generating algorithm is used in communication with an exercise device. Data is input into the processor, such as age, height, weight and sex, and the processor generates an exercise protocol according to a protocol-generating algorithm and the user data. A supervisor is then capable of reviewing and allowing for modification of this exercise protocol.

U.S. Pat. No. 7,074,168 to Fames et al. discloses a system for improving either or both the physical well-being and physical performance of a person, such as in day-to-day activities or sports-related activities. The person's skeletal and muscular characteristics are assessed relative to such things as flexibility, movement, and strength, and the person's performance characteristics relating to an optimized performance of a task or a sports-related activity (e.g., golf swing) are determined. By matching the differences in the person's physical characteristics and performance characteristics, an optimized physical remedial course can be initiated. Also initiated is a remedial course for improving the physical performance by identifying learned defects in performance.

U.S. Pat. No. 7,264,554 to Bentley discloses a system and method for analyzing and improving the performance of an athletic motion such as a golf swing requiring using inertial sensors and video cameras and monitoring a golf swing or such other athletic motion of interest. Analysis includes scoring pre-defined parameters relating to component parts of the motion and combining the parameter scores to yield a single, kinetic index score for the motion; providing a real-time, information-rich, graphic display of the results in multiple, synchronized formats.

U.S. Pat. No. 7,278,966 to Hjelt et al. discloses a system for managing physiological information including a mobile terminal and at least one destination. The terminal is capable of transferring physiological information relating to a terminal user. The destination(s), in turn, are capable of receiving the physiological information and performing at least one operation based upon the physiological information.

U.S. Pat. Nos. 8,287,435 and 8,292,788 to Chapa et al. disclose universal athleticism rating systems and related athletic performance measuring systems for accurately detecting and recording athletic performance. The athleticism rating system evaluates individual athletes against a common, standardized, set of athletic performance tests. Each athlete performs the athletic tests and his or her scores in the individual tests are entered into a standardized calculation to produce a single athletic performance score.

United States Patent Application Publication Nos. 20050014113 to Fleck et al. discloses a system for evaluating a person's athletic ability. The system has a server or a computer system, and several testing locations. The server or computer system includes a database, a central processing unit, and a memory. The database stores results of tests previously subjected to a set of athletes from different physical activities.

United States Patent Application Publication No. 20160220864 to Hollins et al. discloses a method for collecting performance test data during a performance test of an athlete from timing devices associated with a performance test. The method includes automatically receiving an electronic time stamp message from each of the timing devices, each electronic time stamp message incorporating a time stamp generated by the timing device in response to entering into a triggered state during the performance test; and automatically inserting time data corresponding to the received time stamps into respective fields of an electronic performance test record associated with the unique athlete identifier.

United States Patent Application Publication No. 20160027325 to Malhotra relates to improving an athlete's ability to synchronize the movement of their body in time. Certain embodiments provide a feedback system that allows an athlete (or another individual, such as a trainer) to comprehend and optimize the timing of one or more components or features of an athletic movement.

United States Patent Application Publication No. 20170169718 to Smith discloses a computer-based tool that asses an athlete's mental strength to allow the athlete to condition their mind and body for athletic performance. Users engage the tool to self-evaluate one's own mental status after one of three modes. These modes are training, competing and resting.

United States Patent Application Publication No. 20170266498 to Sanders et al. discloses systems and methods for prescribing athletic activity to be performed by a user, and for adapting the prescribed athletic activity based on completed (e.g., ongoing) athletic performances by the user. A coaching plan may be automatically created that prescribes personalized athletic activities as a user trains towards a goal date.

Foreign Patent Publication Nos. EP2263534 and JP2011011058 to Flaction disclose methods for optimizing the training of athletes including measuring, with a portable device, a series of acceleration values during a series of short movements, calculating a plurality of muscular parameters, determining a set of training exercises personalized for the athlete, presenting training exercises to the athlete, and verifying the execution of the training exercises.

Foreign Patent Publication No. WO/2014/197600 to Deangelis et al. discloses systems, methods and software products for the optimized installation and operation of an object tracking system. Performance of the athlete tracking system is continually monitored and optimized based upon one or more of: statically positioned tags, grouping tags within two or more tag sets to assign ping rates, selecting receiver configuration and aim dynamically based upon environmental and situational conditions.

Non-patent publication entitled "Athlete Monitoring" found at http://www.athletemonitoring.com/ discloses data management solutions for coaches, teams and sports organizations for monitoring athlete performance. Another non-patent publication entitled "Kitman Labs" found at https://www.kitmanlabs.com/ discloses an athlete optimization system used for the evolution of athlete performance using data to increase performance and improve player health.

Despite these systems and methods, problems remain in the art for improving an individual's physical or human performance and/or athletic performance on a multi-faceted level while also addressing and/or preventing further injury. In particular, conventional systems and methods fail to provide a multi-faceted approach that analyzes, and continuously monitors, multiple features of an individual's physical or athletic performance, including kinetic, neurological, musculoskeletal ability and aerobic capacity. Further, there remains a need in the art for a system and method that provides sport-specific multi-faceted analysis in combination with using a center of gravity as a point of reference to measure anatomical functions, as well as sports specific movements. None of the prior art systems further provide data points that are determined from the analysis of physical/athletic performance that collects and compares these values against other aspects of health, athleticism, including kinematics, joint kinematics, muscle activation, acceleration, power output, fatigue index, force production, total body control (both gross and fine motor) power, explosiveness, static weight distribution, and cognitive and sensory response as a whole to determine injury risk based on the compilation and combination of said values. Accordingly, a more comprehensive health and/or athletic assessment system and method is needed in the art.

SUMMARY OF THE INVENTION

The present invention provides methods, systems, and computer readable mediums operable to process a continuous stream of data and analysis by software to provide an automated athletic assessment examining an individual and/or athlete's physical performance as well as an individual's injury risk. This physical/athletic performance includes an individual's and/or athlete's individual kinetic, neurological, musculoskeletal ability and aerobic capacity. Assessment and quantification of these performances is used to predict future injuries and generate blueprints of the optimal corrective and health/performance training exercises that correct the athlete/individual's imbalances before injuries can even occur. As used herein, "athletic assessment," "human performance" and/or "physical performance" relates to testing and striving to optimize physical strength, endurance, musculature, joint health for individuals, including athletes, individuals, clients, and/or patients, athletes and/or individuals and/or non-athletes. The subject assessment applies to all individuals, not just athletes, and is adapted to be utilized in fitness centers, gyms and/or health, therapy, or medical centers for customizing assessment of clients and/or patients.

The subject system and method analyzes multiple features of an individual's athletic performance/physical performance, including kinetic, neurological, musculoskeletal ability and aerobic capacity in combination with using a center of gravity as a point of reference to measure anatomical functions. Anatomical function assessment and testing is also needed including rotation, extension, and flexion, among other anatomical functions of every joint. Data points are derived from the analysis of the athletic performance/physical performance or athletic assessment, which are compared against other aspects of athleticism, including kinematics, joint kinematics, muscle activation, acceleration, power output, fatigue index, force production, total body control (both gross and fine motor) power, explosiveness, static weight distribution, and cognitive and sensory response. Assessment and quantification of these performances utilizing a combined algorithm is used to predict future injuries and generate blueprints and protocols of the optimal corrective and performance training and enhancement exercises that will accurately correct the athlete/individual's imbalances before injuries can even occur, catering the performance aspects that coaches want for specific sports to effectively increasing their sport-specific performance.

A system for collecting and analyzing athletic performance/physical performance of an individual and structuring and generating an athletic/rehabilitation protocol is provided. The system comprises one or more athletic assessment and testing devices for performing athletic assessment of said individual comprising kinetic, neurological, musculoskeletal and aerobic capacity of said individual. A digital data storage medium operable with a computer system having a display and a central processing unit (CPU) operable with programming to collect, store and execute programming to analyze said athletic data. The programming is operable to execute one or more analytical algorithm to assess injury risk levels of said individual based on said athletic data. The programming is operable to execute one or more data mining algorithms using artificial intelligence to execute predictive modeling and analytics. The athletic/human performance protocol comprises: (i) information to correct imbalances to treat and/or prevent injuries; (ii) corrective exercises; (iii) performance training exercises; and (iv) protocols to maximize athletic performance/physical performance.

A system for collecting and analyzing athletic performance/physical performance of an individual and structuring and generating an athletic protocol is provided. The system comprises but it is not limited to one or more athletic assessment and testing devices for performing athletic assessment of said individual comprising including kinematics, joint kinematics, muscle activation, acceleration, power output, fatigue index, force production, total body control (both gross and fine motor) power, explosiveness, static weight distribution, and cognitive and sensory response of said individual. Subsequently, the data from these analyses is stored in a digital data storage medium operable with a computer system having a display and a central processing unit (CPU) operable with programming to collect, store and execute programming to analyze said athletic data. The programming is operable to execute one or more analytical algorithm to assess injury risk levels of said individual based on said athletic data as well as their performance levels specific to their sport. The programming is operable to execute one or more data mining algorithms using artificial intelligence to execute predictive modeling and analytics. The athletic protocol comprises: (i) information to correct imbalances to treat and/or prevent injuries and athletic performance/physical performance parameters; (ii) corrective exercises; (iii) performance training exercises; and (iv) protocols to maximize athletic performance/physical performance.

Another aspect of the invention provides a non-transitory computer storage readable medium for collecting and analyzing athletic performance/physical performance of an individual to structure and generate an athletic protocol, comprising computer-useable instructions which, when used by one or more computing devices, cause the one or more computing devices to: (a) generate and receive data from an athletic assessment comprising measuring kinetic, neurological, musculoskeletal and aerobic capacity of said individual and recording athletic data; (b) collect, store and analyze said athletic data; (c) assess injury risk levels of said individual based on said athletic data using one or more analytical algorithm; (d) perform one or more data mining algorithms using artificial intelligence for predictive modeling and analytics; and (e) structure and analyze said athletic data to generate said athletic protocol for said individual, the individual's athletic protocol comprising: (i) information to correct imbalances to treat and/or prevent injuries; (ii) corrective exercises; (iii) performance training exercises; and (iv) protocols to maximize athletic performance/physical performance.

BRIEF DESCRIPTION OF THE DRAWINGS

The invention will be more fully understood, and further advantages will become apparent when reference is had to the following detailed description of the preferred embodiments of the invention and the accompanying drawing, in which.

DETAILED DESCRIPTION OF THE INVENTION

A system, method and computer-readable media are described herein for measuring and collecting data related to health or athletic assessment. The data structure is designed to improve the way data is stored and retrieved in the health or athletic assessment to provide a multifaceted assessment. The one-size-fits-all approach to sports performance is outdated and imprecise. Science-based performance training is provided by way of the subject system and method to enhance technical sports skills and ensure that athletes reach their full athletic potential. After discussing an athlete's specific goals, individualized protocols are developed through the subject system and method, which protocols are both sport-specific and position-specific. Individual athletes are examined through a scientific lens by analyzing his or her individual kinetic, neurological, musculoskeletal ability and aerobic capacity. Using 3D kinematic and motion analysis, the subject system and method is used to identify movement patterns and muscle imbalances that are specific to the athlete's specific sport and position. The subject system and method uses this information to precisely develop individualized training protocols that ensure optimal performance of that athlete and improve timing and accuracy. These protocols may be developed for sport-specific performance.

Optimizing performance of athletes is achieved by way of the subject system and method through measuring and quantifying the subtleties and complexities of athletic movement using sports science technologies. All aspects of athletic performance/physical performance are assessed, ranging from movement patterns of a single muscle to sport-specific movements and reaction times. Results from this analysis are then used to identify areas of imbalances or weaknesses and to develop individualized protocols that maximize athletic performance/physical performance, ensure faster return to play following an injury and prevent future injuries. By uncovering critical, yet overlooked, areas of athletic performance/physical performance, the subject system and method can improve an individual/athlete's performance, helping him/her to stay healthy and avoid injuries. More importantly, the subject system and method helps athletes identify muscle imbalances before they develop into more serious overuse injuries, and therefore have the potential to extend an athlete's career and change the trajectory of athletic performance/physical performance.

The subject system and method provide a comprehensive analysis of an individual athlete or person. Compared to other archaic systems that collect between four to ten different values during an assessment, the system and method collect hundreds of values or data points, for example up to at least but not limited to 1,763 data points. The system and method utilize the center of gravity as a point of reference to measure rotation, extension, and flexion, among other anatomical functions of every joint. These (1,763 data points) values are then compared against other aspects of athleticism, including kinematics, joint kinematics, muscle activation, acceleration, power output, fatigue index, force production, total body control (both gross and fine motor,) power, explosiveness, static weight distribution, and cognitive and sensory response. Generally, no other testing system is as comprehensive or provides as much data and insight into an athlete's performance and risk of injury.

Methodology and technologies are implemented by the system to identify inefficiencies and imbalances throughout the entire kinetic chain, helping athletes improve in every area of athletic performance/physical performance. Athletes are thereby enabled to improve in every area of athletic performance/physical performance. Each athlete is examined through a scientific lens by analyzing every aspect of athletic performance/physical performance, beginning with an athlete's individual kinetic, neurological, musculoskeletal ability and aerobic capacity. Using 3D kinematic and motion analysis, the system and method identify movement patterns and muscle imbalances that are specific to the individual athlete as well as their specific sport and position.

The subject system includes software that analyzes enormous quantities of disparate data from individual athletes to predict future injuries and generate blueprints of the optimal corrective and performance training exercises that right imbalances before injuries can even occur. The subject system relies on artificial intelligence which analyzes the data and utilizes analytical algorithms with a focus on assessing injury risk levels as well as other data mining algorithms using machine learning to improve the system's predictive modeling and analytics. The system automatically generates an automated output with individualized protocols to maximize athletic performance/physical performance, ensure faster return to play following an injury and prevent future injuries. Currently there are no systems that do all three—collect, analyze and generate an output—with precise individualized training, which are also sport-specific and position-specific, and ensure optimal performance of that athlete by improving timing and accuracy, together with proactive pre-habilitative exercise and recovery methods that improve the range of motion, reduce the risk of injury and maximize performance.

The global assessment and artificial intelligence software of the subject system preferably includes the following evaluations alone and/or preferably in combination: (i) Orthopedic and physical evaluation; (ii) Full body composition bio-analysis that uses various technologies and/or diagnostic principles (i.e. impedance, FLIR.); (iii) Motion-capture capabilities that use 2D markers or 3D sensors to analyze bio-mechanic and kinematic markers; these data will then be used to provide a thorough analysis of an athlete's functional movement and/or sport-specific movement sequence; (iv) Surface EMG sensors that analyze muscle activation patterns. This technology will complement the kinetic/bio-mechanic testing technology; (v) Dynamic gait analysis that will collect data on static weight distribution and pressure mapping of the athlete's feet to determine their biomechanics and predict the risk of injury; (vi) Force plate technology that measures ground reaction force, landing force, functional max force L/R ratio, eccentric and concentric force, L/R ratios, and other variables that affect force production by the lower body during various movements (e.g. countermovement jump, squat jump, mid-thigh pull and static balance); (vii) Isokinetic extremity testing technology that measures various aspects of kinetic power output. This technology uses 22 pre-programmed and 15 proprietary isokinetic, isometric, and isotonic exercises to evaluate and strengthen every muscle group adjacent to the joint of interest. This technology measures torque/power, range of motion, fatigue index, work per repetition, total work done, and force decay. The data collected using isokinetic extremity testing technology will be used during the assessment and during every training session to measure progress over time; (viii) Free space reaction time and agility analysis technology that combines a 3D-rendering camera that captures up to 32 anatomical points to create a visual prompt avatar, a heart rate monitor and neuro-motor responses with the proportional values for speed, acceleration, deceleration and reaction time in an 8-direction vector (forward, back, left, right, forward left/right, backward left/right.); (ix) Neural efficiency technology that uses a combination of kinetic, auditory and visual cues to assess and train timing, rhythm, and coordination via synaptic responses to stimuli. This technology measures in milliseconds the difference in time between the stimulus and the athlete's reaction. Brain mapping will be used to identify regions in the brain that may not function optimally and thus pinpoint the underlying causes of deficiencies in physical and cognitive performance; (x) Sensorimotor skill technology that uses ten exercises to analyze basic and specific sensory and motor skills. The athlete's data are compared to those of other athletes to eye-hand coordination, depth perception, visual acuity, target capture, perception span, multiple object tracking, contrast sensitivity, near/far quickness, and reaction time. The subject system and method uses its own proprietary exercises and a combination of technologies to provide a complete and customized analysis of neuro-cognitive and motor skills and to provide individualized corrective protocols; (xi) Eye tracking technology that will be able to adapt, analyze and interpret visual skills and conditions that impact performance. This eye tracking technology can also reproduce various sight-related situations and conditions that impact performance; (xii) Cardiopulmonary diagnostic technology that will measure heart rate, breathing rate, VO2 max, and maximum oxygen usage efficiency. This technology can be combined with cardio-pulmonary training technology that simulates changes in altitude and oxygen concentration and forces the cardiopulmonary system to adapt to variable conditions; and (xiii) Concussion assessment and return-to-play technology that combines heart rate, cognitive response, balance (using the BESS test), motor response, reaction time and speed, and eye-tracking technology.

Combinations of these assessments and tests provide an automated athletic assessment and testing system that examines an athlete through a scientific lens by analyzing every aspect of athletic performance/physical performance to predict future injuries and generate blueprints of the optimal corrective and performance training exercises that right imbalances before injuries can even occur.

The subject system and method combine science, innovation and specialized training to suit each athlete's individual needs. The one-size-fits-all approach to sports performance is outdated and imprecise. Today, the best athletes and teams approach their training based on the unique needs of each athlete, which vary according to sport and position. By focusing on science-based performance training to enhance technical sports skills, the subject system and method ensure that athletes reach their full athletic potential. After discussing an athlete's specific goals, the subject proprietary protocols are used, which are both sport-specific and position-specific. Each athlete is examined through a scientific lens by analyzing his or her individual kinetic, neurological, musculoskeletal ability and aerobic capacity. Using 3D kinematic and motion analysis, the subject system and method identifies movement patterns and muscle imbalances that are specific to the athlete's specific sport and position. This information is used to precisely individualize training that ensures optimal performance of that athlete and improves timing and accuracy.

Figure 1:
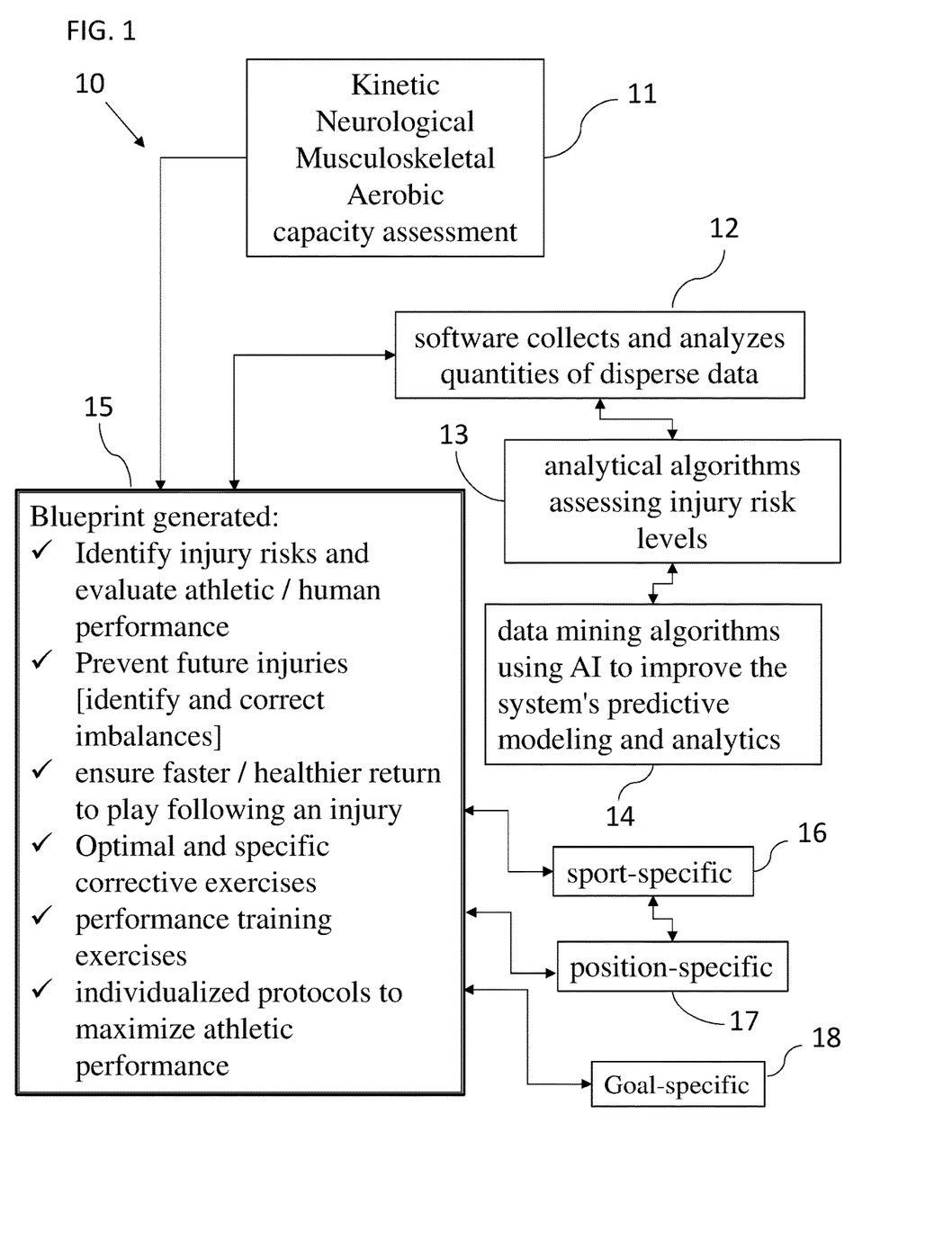
FIG. 1 illustrates a flow chart of an embodiment of the subject system and method.

FIG. 1 illustrates a flow chart of an embodiment of the subject system and method, shown generally at 10. One or more athletic assessment device is utilized to perform an athletic assessment of the individual at 11. The assessment includes kinetic, neurological, musculoskeletal and aerobic capacity of the individual. assessments more specifically include body composition, orthopedic evaluation/musculoskeletal, biomechanics, neurological/sensory motor skills, aerobic/anaerobic, and/or capacity assessment and testing. At 12, software collects and analyzes large quantities of disparate objective data. As the health/physical performance/athletic data is collected, it is stored and analyzed using software and digital data storage medium operable with a computer system having a display and a central processing unit (CPU) operable with programming. The programming is operable to execute one or more analytical algorithm at 13 to assess injury risk levels of the individual based on the athletic data. These analytical algorithms process and assess injury risk levels+performance. The programming is operable to execute one or more data mining algorithms at 14 using artificial intelligence to execute predictive modeling and analytics. An athletic protocol or blueprint is generated at 15. The protocol or blueprint 15 comprises: (i) identify injury risks and evaluate athletic/human performance; (ii) prevent future injuries [identify and correct imbalances to treat and/or prevent injuries]; (ii) ensure faster/healthier return to play following an injury; (iii) optimal and specific corrective exercises; (iv) performance training exercises; and (v) individualized protocols to maximize both individual and athletic performance/physical performance. The athletic assessment and protocol may be sport-specific 16, position-specific 17 and/or goal-specific 18.

For example, a sport-specific protocol generated by the subject system and method may be directed toward baseball and/or softball. The protocol, for example, may include: 1) sensory strobe training and eye hand coordination training to improve batting average; 2) hitting for power: Training using Isoinertial technology to develop maximum rotational torque capability throughout the swing phase, driving the ball in the gaps with authority; 3) fielding: Develop involuntary fielding mechanics and fast hands producing fewer errors and an increased fielding percentage by footwork, agility, sensory strobe, and eye-hand coordination training; 4) running: Enhance sprinting kinematics for optimal running mechanics and efficiency using clinically proven Whole Body Vibration+3D Sports Simulation.

Figure 2A:
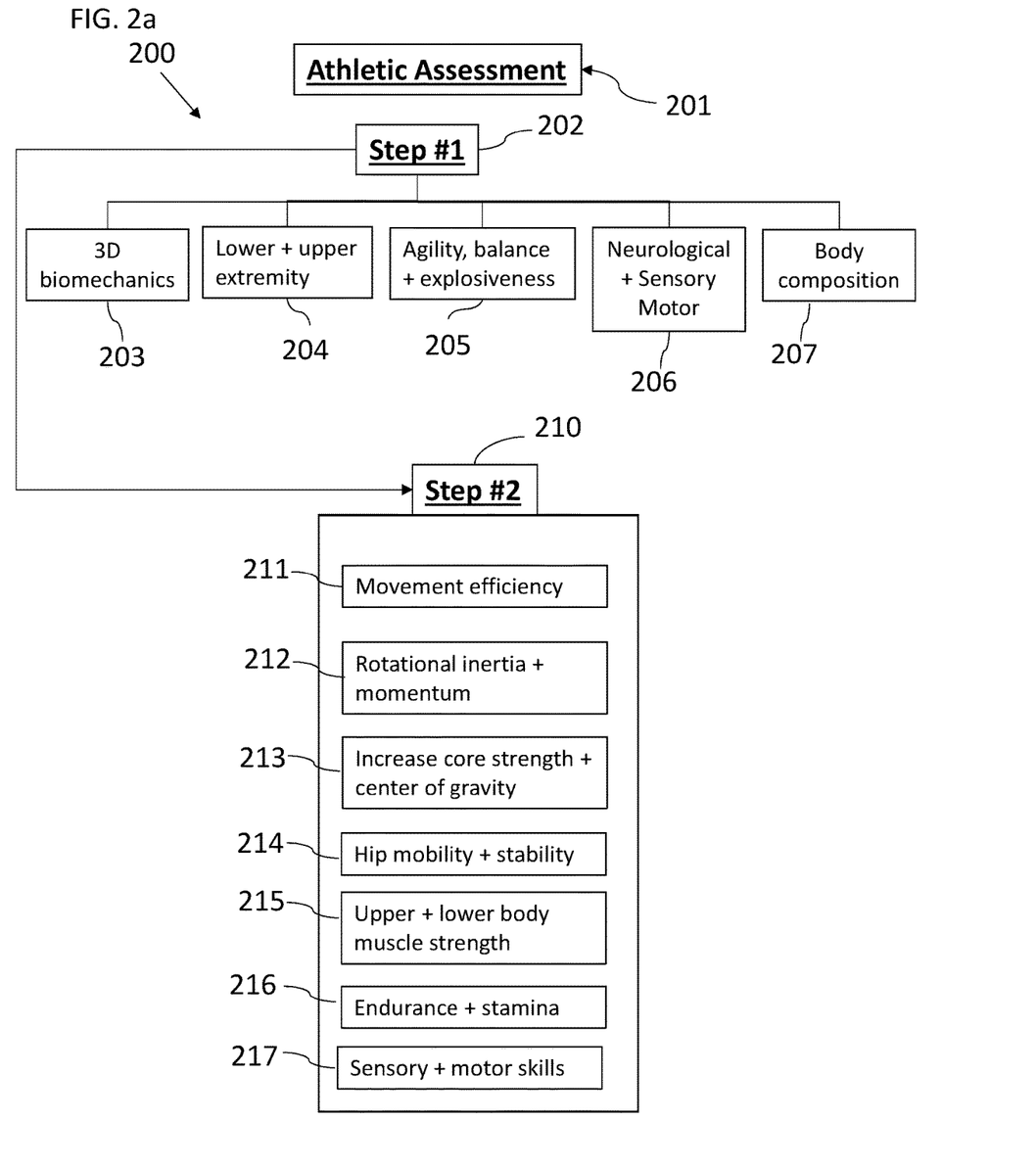
FIG. 2*a* illustrates another flow chart of an embodiment of the of the subject system and method, showing an embodiment of Steps #1 and #2.

Another example of a sport-specific protocol generated by the subject system and method may be directed toward basketball: 1) reaction time+awareness: basketball players need to anticipate where players will be and react to their movements on the court (open lanes, back door cuts, slash, defensive slips); 2) hand-eye coordination: basketball players must have the ability to react when the ball comes their way. The split-second decisions a player makes can make or break a game; 3) power/speed/explosiveness: the ability to drive to the basket passed a defender, stepping through the lane for a steal, getting back on defense, full court presses, fast breaks, rebounding, shooting, etc. are all fundamental skills basketball players need. FIG. 2a illustrates another flow chart of an embodiment of the subject system and method, showing Steps #1 and #2, shown generally at 200. An athletic assessment using one or more athletic assessment device is carried out, shown generally at 201. The athletic assessment preferably includes a three-step assessment to determine kinetic, neurological, musculoskeletal and aerobic capacity of the individual. In step #1 of the assessment, shown generally at 202, the following assessments and tests are carried out: (i) 3D biomechanics, +kinematics of movement, kinematics of running/movement, objective kinetic and kinematic assessment for functional movement, kinetic and kinematic assessment for sport's specific movements (sport/position based), Davenport and Euler angles, segmental, acceleration, mean angles achieved, EMG muscle activation, Jumping and landing mechanics, and/or orthopedic evaluation for pain and functionality (A) at 203; (ii) lower+upper extremity testing including at least one or more of Orthopedic+Physical therapy, evaluation based on sport and position, Range of motion, Power outputs+Explosiveness (torque, lbs/s, lbs, d/s, watts, kg, kg/s percentages), Fatigue Index, Work per repetition and work done, Power decay, L/R ratios and deficits, Peak Torque and all its variables (time to peak torque, joint angle for peak torque, torque time held), Agonist/antagonist muscle ratios, Rate of force development/Maximum Force, Total, L/R percentage of concentric and eccentric force produced in isokinetic, isotonic and isometric testing, Specific Left or Right force production/strength Dynamic and static gait analysis at 204; (iii) agility, physiological capacity+balance and explosiveness, including at least one or more of Proportional acceleration in 8 directions, Proportional deceleration in 8 directions, Proportional speed achieved in 8 directions, Reaction time to lateral movement in 8 possible directions lateral deficits, Variable heart rate, VO2 Max aerobic capacity, Lower body balance (anterior, medial and lateral hip movement/knee strength), BESS test (Balance Error Scoring) System, LESS (Landing score system), Brain waves and brain mapping assessment, Metabolic profiles (glucose, hydration, metabolites and electrolytes) at 205; (iv) neurological+sensory motor skills assessment including one or more of brain timing, brain mapping, sensory motor skills (visual clarity, perception span, depth perception, peripheral/central vision. Eye/hand coordination, go/no go, multiple object tracking) at 206; and (v) Body composition including at least one of Total body weight, total water (intracellular/extracellular), Lean body mass and body fat (lbs/%), Basal metabolic rate, Loss/gain recommendations, and/or Segmental body mass (lbs) at 207.

In step #2 of the assessment, shown generally at 210, analysis of data is carried out, including assessments generating at least 1763 reference data points to be analyzed. Assessments carried out include: movement efficiency at 211; rotational inertia+momentum at 212; increase core strength+center of gravity at 213; hip mobility+stability at 214; upper+lower body muscle strength at 215; endurance+ stamina at 216; and sensory+motor skills as 217. Movement efficiency 211 preferably includes one or more of the following evaluations: Functional movement: Bilateral scoring for 11 functional movements; giving a 1-3 scoring for a total score of 42 points (the higher the number, the more efficient the movement was and the lower injury risk will be); LESS testing: scoring an overall 1-3 points (3 being the best outcome); Y Balance, Anterior, postero-lateral and posteromedial aspects scored and compared bilaterally and then averaged for a percentage of comparison between sides. Benchmarks are in place for injury risk determination based on scoring and data combination; Orthopedic+Physical therapy complete evaluation by PT+ROM objective determination (PT Evaluation+Isokinetic testing); 3D motion analysis for all functional movements involved in this assessment for objective data recorded (mean and Davenport angles, EMG muscle activation); 3D motion analysis for all sport-specific movements involved in this assessment for objective data recorded (mean and Davenport angles, EMG muscle activation, segmental acceleration in). Increase core strength+center of gravity 213 preferably includes one or more of Orthopedic+Physical therapy evaluation by PT/Sports Physiotherapist performing at least one of Sports specific evaluation, Range of motion and functionality, Muscle-skeletal integrity and functionality, and/or Pain evaluation (pain=not allowed to perform the assessment).

Figure 2B:
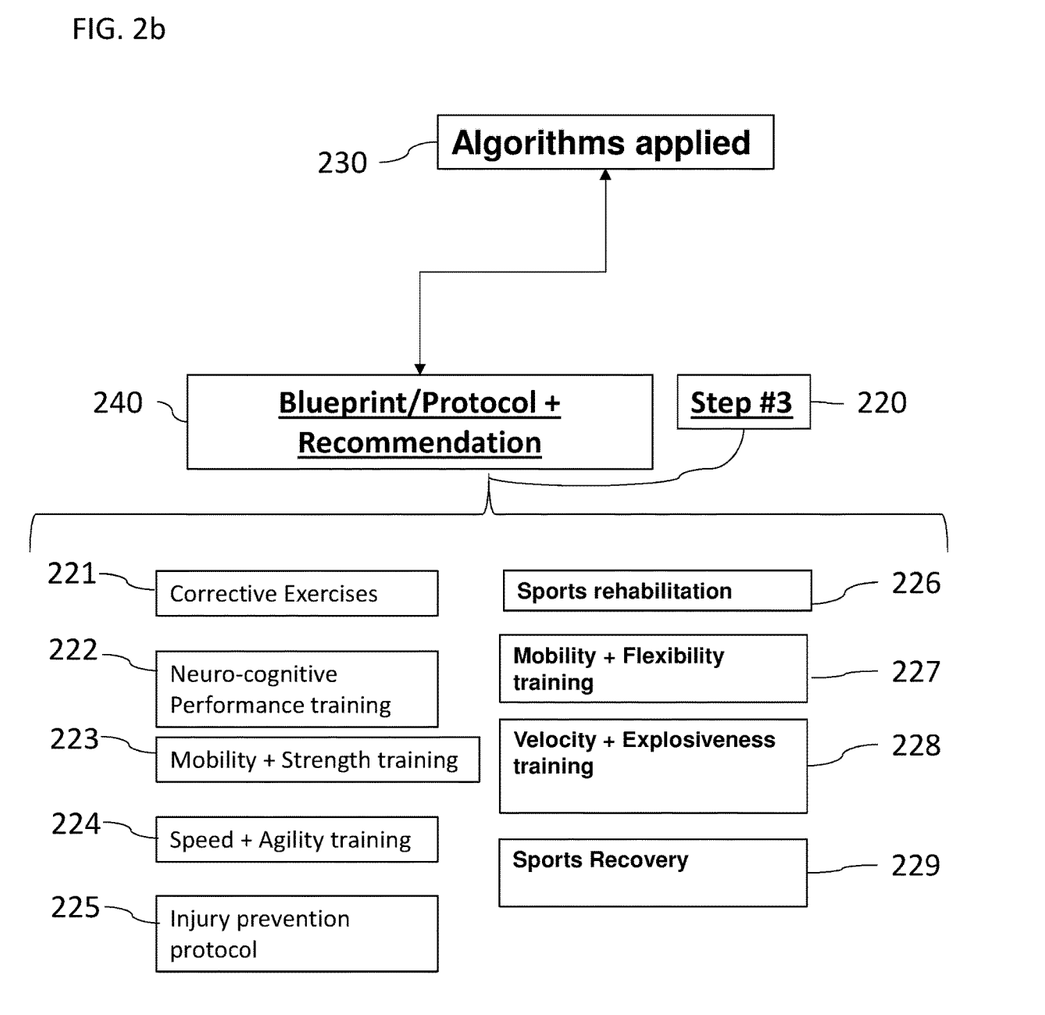
FIG. 2*b* illustrates Step #3 of the flow chart of FIG. 2*a*.

FIG. 2b illustrates Step #3 of the assessment, continued from FIG. 2a. A blueprint/protocol and recommendation is generated at 240 and implemented in Step #3 of the assessment, shown generally at 220. Assessments are recommended, and protocols customized: corrective exercises 221, neuro-cognitive performance training 222, mobility+ strength training at 223, speed+agility training 224, injury prevention protocol 225, sports rehabilitation 226, mobility+ flexibility training 227, velocity+explosiveness training 228, and/or sports recovery 229.

Algorithm 230 is applied to the assessment data. The algorithm 230 applies a full combination of more than 20% L/R ratio+>25% deficit on isokinetic+>10% imbalance on Y balance+<15 points on FMS+>20% deficit in deceleration+ Non optimal gait scan=will result in Substantial risk of injury. However, these aspects do have a hierarchy in importance, i.e., if the athlete presents only >25% deceleration deficit+>25% isokinetic deficit=Substantial injury risk. In the same fashion, if Y balance <2%+20% isokinetic=moderate injury risk. Ten (10) tests that result in a score of 10 possible points (Deficient=2 points, below average=4 points, average=6 points, above average=8 points, Optimal=10 points)=The highest number of points give a composite score out of 100 points; an injury risk predictor score is directly linked to the composite score, with the highest composite=lowest injury risk.

Athletic data is collected from the assessment 201 which is stored and analyzed using a digital data storage medium operable with a computer system having a display and a central processing unit (CPU) operable with programming. The programming is operable to execute one or more analytical algorithm at 230 to assess injury risk levels of the individual based on the athletic data. The programming is operable to execute one or more data mining algorithms using artificial intelligence to execute predictive modeling and analytics. An athletic protocol or blueprint is generated at 240 that includes: (i) information to correct imbalances to treat and/or prevent injuries; (ii) corrective exercises; (iii) performance training exercises; and (iv) protocols to maximize athletic performance/physical performance. The athletic assessment and protocol may be sport-specific and/or position-specific.

Figure 3:
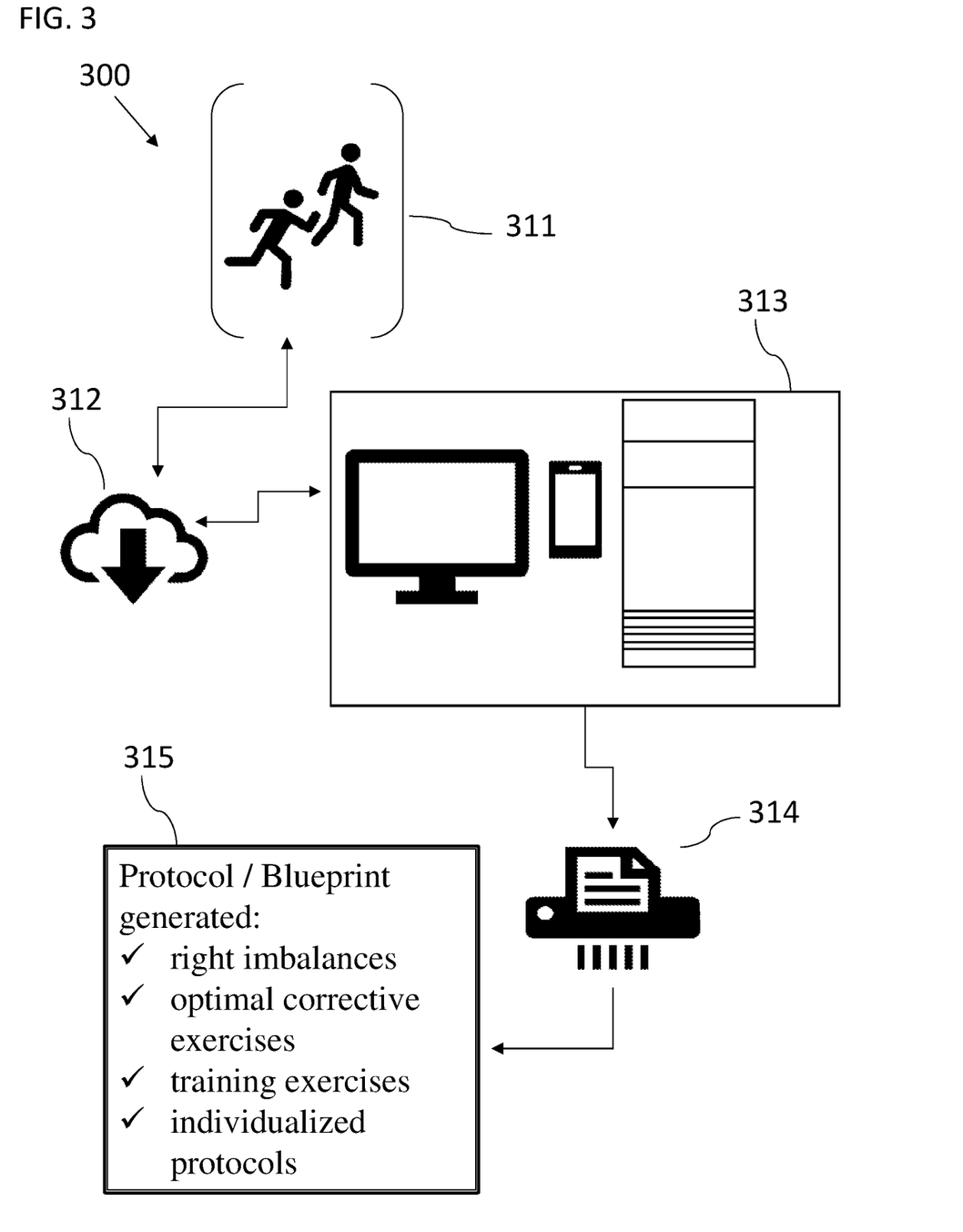
FIG. 3 shows a structural flow chart of an embodiment of the subject system and method.

FIG. 3 illustrates a flow chart of an embodiment of the subject system and method, shown generally at 300. One or more athletic assessment device is utilized to perform athletic assessment of the individual at 311. The athletic data is collected, stored and analyzed using a digital data storage medium operable with a computer system having a display and a central processing unit (CPU) operable with programming, shown generally at 313. The data may be collected and stored using a wireless network as shown at 312, in communication with the local CPU 313. The programming is operable to execute one or more analytical algorithm to assess injury risk levels, compare data, and carry out data mining algorithms using artificial intelligence. An athletic protocol or blueprint is generated at 314, which may be formed as a table 315 and includes information to correct imbalances to treat and/or prevent injuries; corrective exercises; performance training exercises; protocols to maximize athletic performance/physical performance.

Multiple athletic assessment and testing devices are adapted to be utilized in the subject system and method, including for non-limiting example:

3D Motion tracking software is utilized to analyze sport-specific motion to provide a detailed analysis of an athlete's biomechanics to determine how the kinetic chain is functioning. Muscles, connective tissues, joints, bones, nerves, and gravity, all work together like links in a chain to create a delicate system that ideally works effectively and efficiently. Healthy biomechanics enable efficient movement by properly supporting all the elements of the kinetic chain. On the other hand, poor biomechanics cause the body to overcompensate for failing links, resulting in increased energy expenditure, muscle fatigue, and pain. This leads to poor habit formation, poor muscle memory and the continuation of poor biomechanics. Quantitative results from the 3D motion and kinematic assessment allow analyzation of movement patterns and identification of biomechanical inefficiencies, as well as muscular imbalances that may be invisible to the human eye or that may go undetected. The subject system and method is appointed to be utilized in conjunction with a team of experts that work closely with coaches, trainers, and parents for correcting an athlete's structural deficiencies, thus ensuring that the athlete performs at optimal level.

EMG muscle response analysis is carried out preferably by way of Electromyography Surface EMG to accurately assess symmetry, synergy and sequencing of single muscles and muscle groups. The technology measures small electrical impulses that are transmitted along muscle fibers during the contraction and relaxation of the athlete's muscles during sport-specific movements. These measurements are used to identify the sequence and biomechanical patterns of that muscle's activation and movement. The information obtained by surface EMG technology is used in determining the most appropriate prehabilitation, rehabilitation and/or training formulas to improve movement efficiency, reduce muscle fatigue, correct dysfunctions, muscle imbalances and prevent injuries. The benefits to athletes include improved performance, injury prevention, reduced muscle fatigue, and faster rehabilitation.

Neurotechnology, brain training, preferably utilizes Interactive Metronome (IM). IM technology combines principles of music, sports and neuroplasticity to improve focus, concentration, coordination and timing. It can also be used to improve language processing, reading and math fluency, and control of impulsivity/aggression. Correct timing and coordination are crucial to athletic success because even the smallest errors in timing can make a difference between victory and loss. The IM provides a training program that involves matching various motor activities with the beat of a metronome while measuring the timing accuracy within milliseconds. This technology improves connectivity and communication between the different task-oriented structures in the brain, resulting in to adapt one's movements to specific conditions, tasks, and environments, making the coordination between the mind and the muscles easier, and as a consequence, more effective. This unique technology is used by hundreds of professional athletes such as professional golfers Vijay Singh and Glen Day, as well as professional sports teams, to gain mental precision in timing and the transmission of messages along the neural pathways, effectively gaining a competitive edge.

Another device implemented by the subject system and method includes the AlterG Anti-Gravity Treadmill. The system uses NASA-patented differential air pressure unweighting technology to reduce the users' body weight by as much as 80 percent. This reduces the risk of stress injuries caused by weight-bearing activities and helps speed up the recovery process. Particularly for users with lower extremity injuries, physical therapy, and other rehabilitation methods often have to be delayed because weight-bearing activities and high impact activities such as walking or running can exacerbate the injury. Since the Alter G treadmill eliminates the difficulties associated with body weight, it can be used early in the rehabilitation process to normalize gait mechanics, and safely perform aerobic conditioning without the risk of aggravating the injury.

Isokinetic Extremity Testing+Rehab: The Isokinetic extremity machine is generally considered the ultimate tool for measuring and improving physical/human performance in athletes. It uses 22 standard test and exercise patterns to precisely measure muscle imbalances and inefficiencies from one extremity to the other in various positions. It is so accurate that the NFL has decided to implement isokinetic strength testing as a mandatory component of the Combine. This "lie detector" of muscles and muscle groups helps the subject system and method to uncover areas of weaknesses that inhibit performance and increase the risk of injury. The assessments performed on the Isokinetic Extremity machine are designed to quantify mobility, stability, control and strength. Scientific studies have proven that this technology is effective at reducing pain, improving muscle strength, increasing the velocity of muscle recruitment and stabilizing the joints, all of which are essential for efficient movement and injury prevention.

3D Sports Simulation Training: 3D Sports Simulation can simultaneously track the integration of the brain, heart, and body while moving in free space. It uses clinically inspired models to measure various aspects of movement to evaluate sport-specific abilities. The simulator mimics the unpredictable gameplay by displaying visual cues that the athlete must react to while measuring moment-to-moment reaction time, acceleration, speed, distance traveled and heart rate. Currently, most coaches rely on a stopwatch to test for speed and reaction time. By testing the athletes' stamina, balance and coordination, visual perception and mobility, the 3D Sports Simulation Technology provides more precise and objective data, allowing coaches and trainers to design better programs that result in improved performance.

3D Baseline Concussion Assessment: 3D Baseline concussion assessment is considered on of the most accurate concussion detection system in the industry. While 300,000 sports-related concussions are diagnosed annually, it is estimated that approximately one-third of athletes have suffered undiagnosed concussions. Since the effects of concussions add up over time, it is critically important to diagnose them early and ensure that athletes are sufficiently recovered before returning to their sport. The subject system and method, therefore, provides an accurate and sensitive method of concussion assessment. The 3D Sports Simulation Technology immerses the athlete in a simulated environment that collects and analyzes 3-dimensional movement responses (pre and post-concussion) and identifies deficits in neurocognitive testing following an injury. It looks at depth perception, visual acuity anticipation skills, and peripheral awareness. Because movement responses and reaction times are unique to each athlete, the baseline assessment/athletic assessment of the subject system and method compares the data pre- and post-concussion and determines the extent of the injury and best course of treatment for each athlete.

During intense physical activities, the joints and muscles get overused, resulting in fatigue of the joints and the tearing of muscle tissues. Whole Body Cryotherapy is the preferred technique for faster recovery after periods of physical training. Cryotherapy, translated as "cold cure" exposes the body to a controlled temperature that ranges from minus 166 to minus 274 degrees Fahrenheit for 3 minutes. The extremely cold temperature activates the body's fight-or-flight reaction, ensuing vasoconstriction and the consequent reduction in the production of molecules that are the cause for inflammation. After the treatment, the body immediately reheats and vasodilation occurs, flushing the muscles with oxygenated blood, thus speeding up the healing process. Cryotherapy works by the temporary numbing of the nerve endings that report to the brain that there is pain in joints or muscles while also inducing the release of endorphins (aka. feel good hormones) that endow athletes with the mental fortitude to train harder, longer, and at a higher frequency.

Another assessment and testing tool or device includes localized cryotherapy, which is similar to whole body cryotherapy, but it targets a specific muscle area or spasm. Therapy is applied with a localized device, which disperses cold air that reaches −25 to −40 Celsius by a precision hose, which cools the affected area. Localized cryotherapy is more powerful and effective than traditional icing and takes between 3 to 5 minutes per session, compared to 10 to 15 minutes of icing. Localized Cryotherapy works by the temporary of the nerve endings that report to the brain that there is pain in numbing joints or muscles while also inducing the release of endorphins (aka. feel good hormones) that endow athletes with the mental fortitude to train harder, longer, and at a higher frequency.

Various technologies may be implemented and/or utilized, including for nonlimiting example:

Pneumatic Compression Pulse Technology: Pneumatic compression sequential pulse technology uses massage therapy in sports medicine. Compression massage therapy is one of the most effective recovery tools for athletes who want maximum performance and accelerated recovery. This method has been proven to increase blood circulation and lymphatic drainage, as well as to reduce both muscle swelling and fatigue. This patented device, which is based on three distinct massage techniques, stimulates blood flow out of muscles, allowing metabolites that are the cause of pain and inflammation to be flushed out of the tissue. This device uses dynamic compression that mimics the natural flushing pulses of the muscle. These pulses move from the extremities upward to prevent the backflow of blood, speeding up the removal of waste products, such as lactic acid, that are created in the muscle during intense exercise. If the compression therapy is used before exercise or before a game, it will aid in the warm-up process of the muscles, effectively helping reduce the risk of. Athletes have reported feeling refreshed and less sore after using the compression, which allows them to return to training faster and, thus maximizing their performance extensively injury.

Isoinertial Technology: Isoinertial training is a training technology that uses the principles of strength training, but uses a flywheel, which allows the muscles to work through a wider range of motion at the maximum capacity than traditional weight training. Flywheel training maintains constant inertia throughout the range of motion, allowing the muscles to work at the maximal force at every angle. Flywheel training also allows the muscles to work under eccentric overload or the downward portion of an exercise. Eccentric exercises are often under-utilized by athletes, but provide great benefits for muscle strength, as muscles are approximately 30% stronger in the eccentric phase than in the concentric phase (the upward motion of the muscle). Eccentric exercises also strengthen the connective tissue around the muscles, improve flexibility and reduce muscle soreness in the future. Scientific studies have shown that this type of training stimulates more muscle growth and strength and results in a higher degree of muscle activation by the nervous system compared to traditional weight training. This technology, therefore, helps athletes improve their strength and flexibility and results in optimal performance while reducing the risk of injury.

Force Plate: Force plate analysis measures ground reaction forces generated by the body. The force plate has been clinically proven to quantify balance, gait, and other parameters of biomechanics. In addition, force plates have been regularly used in research and clinical studies, in examining balance, gait, and sports performance. Force plates are being used as measuring instruments for leading professional sports teams, such as the Atlanta Falcons. In measuring athlete's explosiveness, the force plate calculates acceleration, work, power output, jump angle, and jump distance. The data provided by the force plate can determine the torque, work, and power of each joint. Most recently, the force plate has been used at the NFL Combine in analyzing player's vertical jump. By jumping as high as they can while standing on the platform, the plate determines how much force is being exerted. This analysis can be the difference in selecting one player over another, as it provides important information about a player's athletic abilities. The force place analysis also identifies players whose body composition and dynamics suggest that they will be able to play NFL football at a high level for an extended period of time.

Cardiopulmonary V02 Max: The VO2 Max Assessment is an indicator of cardiovascular fitness. The test is based on the premise that the amount of oxygen used by muscles is relative to the intensity of exercise. The technology used by the subject system and method aids in the uncovering of fitness deficiencies by analyzing expired gases during exercise to customize training plans and formulas aimed to improve aerobic endurance and ensure optimal performance while reducing the risk of injury.

Super Pulsed Laser Technology: Super Pulsed Laser technology is designed to get athletes back in the game quickly following an injury and has been scientifically proven to be effective in treating sports injuries. Trauma from sports injuries and intense exercise stimulates the release of chemicals that cause inflammation, which in turn, may cause damage in the long term to soft tissues and may predispose athletes to develop early-onset arthritis and degenerative damage in the joints. Super Pulsed Laser emits brief pulses of light onto damaged cells, where photons of light stimulate a series of cellular reactions to produce enzymes, increase blood and lymphatic flow and stimulate collagen production, which in turn, accelerates tissue healing, reducing inflammation, thus shortening the rehabilitation time from injuries, as well as the recovery time between workout sessions.

Marc Pro Muscle Recovery is an effective muscle stimulator that reduces muscle fatigue and soreness, speeds up recovery and results in a faster return to play. The technology improves physiological function of muscles by stimulating muscles that are difficult to contract while preventing discomfort and fatigue. The device works by applying small electrical currents to the muscle, which stimulate muscle contractions. Unlike most other muscle stimulators, which cause quick and strong muscle contractions that are often painful, it uses scientifically backed settings to comfortably contract and then slowly relax muscles in a manner that simulates active recovery. These gentle muscle contractions improve blood and lymph flow, deliver nutrients to the muscles, remove waste products and stimulate tissue repair after intense exercise.

Sensory Performance: The Sensory Station uses principles of neuroscience to assess and train an athlete's sensory system and improve performance. Coordination between the sensory and motor systems is essential for athletic performance/physical performance. An athlete's ability to assess his or her environment, estimate distance and perceive objects in the peripheral vision can make the difference between winning and losing. The Sensory Station assesses ten visual and sensory-motor skills, including depth perception, eye mobility, peripheral and central vision, reaction time and eye/hand coordination. The station also measures the speed at which visual information is acquired and how quickly attention can shift from near to far objects. These measurements are then compared to a large database, which includes information from athletes of all levels and abilities, to identify any weaknesses that may exist. The subject system and method's algorithm analyzes the results and devises a training program to improve any deficiencies. Studies have shown that this science-based approach to visual training not only improves sports performance but can also reduce the risk of concussions. The subject system and method uses this advanced technology to ensure that each athlete reaches their full potential and reduces the risk of injury.

Dynamic Visual Stimulus Technology: Dynamic visual stimulus technology is a motion simulation device that utilizes sequential LED lights to both assess and train an athlete's depth perception, focus, concentration, eye/hand coordination, eye/foot coordination, reaction time, stimulus anticipation, and timing during sport specific movements. Using visual stimulus at different speeds up to 100 mph and configurations while collecting real-time data, customized measurable routines can be created, both on an individual and team basis. It is a training technology device for a wide range of reaction time/anticipation response training, vision training and numerous other cognitive and technical skills training that traditional training cannot replicate. Utilizing a combination of patent-pending hardware, software, and electronics to rapidly increase the user's development in all areas allows each athlete to set a personal benchmark based on tangible feedback at every training session.

Sensory Goggles: Visual acuity is essential for athletic performance/physical performance. The subject system and method use visual information to estimate the distance and speed of objects and to coordinate movements. Even small deficiencies in vision can have an impact on athletic performance/physical performance. Despite the common perception that senses are fully developed in childhood and decline later in life, recent research has shown that the brain has a remarkable capacity to train and improve senses. Strobe goggles are designed to train the connections between the eyes, brain and body. This advanced technology uses liquid crystal technology that allows lenses in goggles to alternate between clear and opaque states several times a second. These brief periods of blocked visual input result in improved vision, attention and the ability to anticipate the timing of moving objects. By improving visual abilities, strobe goggles can improve athletic performance/physical performance and reduce the risk of injury.

Quick Board: The Quick board is an agility trainer. The Quick Board increases agility, quickness, and reaction. It provides real-time feedback via the iPad using objective data, which results in significant performance increases. This feedback enhances the proprioceptive benefit of exercises by performing tasks with the head up in order to fully restore pre-injury communication. In addition, the Quick Board is the only device that provides the capability and method to test+train lower extremity coordination, which can reduce exposure to injuries. The Quick Board Bilateral React Drill is vital in tracking an athlete's speed by monitoring for over training. The testing portion of the Quick Board highlights asymmetry due to dominancy or previous injury. It also captures baseline data for critical return to play decisions. Additional benefits include increased bilateral reaction and proprioception.

Neuropriming: The Halo Sport is a wearable fitness device that works through a process called Neuropriming. Neuropriming is the process of using neuro-stimulation during athletic training to build stronger, more optimized connections between the brain and the muscles. Neuropriming introduces a state of hyper-learning or "hyperplasticity" in the brain, which refines the brain's ability to learn and adapt to athletic training. This allows athletes to see better results, faster. Athletes wear Halo Sport before or during training, and the device's soft foam primers deliver electrical stimulation to the brain's motor cortex. This increases neuroplasticity, which accelerates the optimization of neuromuscular circuitry through training. Improved neuromuscular output leads to more precise, coordinated, and/or explosive movement whichever the athlete targets during training.

Visual Stimulus Technology: The technology is a wireless reaction training system comprised of LED powered lights. The lights act as targets for the user to touch and can be adapted and configured for all sports-specific exercises. This training system is designed to capture physical/human performance, targeting reaction time, speed, agility, and coordination. Using real-time data, the subject system and method performance training program incorporates Fitlight technology by creating customized measurable routines both on an individual and team basis. It is used as a powerful training technology for a wide range of physical conditioning, reaction/response training, vision training and numerous other physical and cognitive skills training.

Altitude Training System: The Altitude Training mask is designed to simulate low-oxygen altitudes. This technology can mimic altitudes up to and beyond 15,000 feet. This system is great for athletes that are currently injured or rehabbing, as it allows for a proper cardiovascular workout. By maintaining and increasing aerobic capacity levels while injured, the system's exercise scientists, strength and conditioning coaches, and performance enhancement specialists can focus on reconditioning and work on sport-specific skills. This makes the transition back to the field much easier. Most importantly, it allows the athlete to train harder and recover faster. The system can also be used for weight training, as the altitude environment will increase their muscle mass, strength and endurance. Combined with the Alter G Anti-Gravity Treadmill, the Altitude Training Mask can significantly increase cardiovascular output, while reducing the impact on the body and joints. This allows for improvement in fitness levels while rehabbing at the same time. This can also benefit athletes by preparing them in competitions at specific altitudes, all while simulating the oxygen environment.

Isoinertial Training: Isoinertial training increases strength training efficiency by applying the inertia of a flywheel to create optimal resistance. Designed for resistance training in space, this exercise device maximizes performance while reducing the risk of injury.

Isokinetic Testing Rehab: The Isokinetic machine uses tests and exercise patterns to identify muscle imbalances that inhibit performance and increase the risk of injury. This technology also improves muscle velocity and shoulder strength in baseball players.

3D Sports Simulation Technology: 3D Sports Simulation Technology mimics gameplay while measuring reaction time, acceleration, speed, distance traveled and heart rate. The system benefits athletes by improving performance, reaction time and hand-eye coordination.

Sensory Performance Training: Sensory performance training uses principles of neuroscience to train an athlete's sensory system. It tests and improves an athlete's visual and sensory-motor skills. This technology develops better hand-eye coordination, depth perception and faster reaction time.

Neurotechnology: This cutting-edge performance technology works by improving connectivity and communication in the brain, resulting in improved focus, concentration, coordination, decision-making and reaction times, better decision making and reaction time.

Balance+Footwork Training: Balance and footwork training includes drills and exercises aimed at creating a more stable body, improved coordination, agility, reaction time and proprioception, helping athletes become faster, more efficient, and less prone to injuries.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:
1. A system for collecting and analyzing physical performance of an individual and structuring and generating an athletic protocol, comprising:
   a. one or more athletic assessment and testing devices for performing athletic assessment of said individual comprising kinetic, neurological, musculoskeletal and aerobic capacity of said individual and recording athletic data;
   b. a digital data storage medium operable with a computer system having a display and a central processing unit (CPU) operable with programming to collect, store and execute programming to analyze said athletic data;

c. said programming operable to execute one or more analytical algorithm to assess injury risk levels of said individual based on said athletic data;
d. said programming operable to execute one or more data mining algorithms using artificial intelligence to execute predictive modeling and analytics;
e. said athletic protocol comprising: (i) information to correct imbalances to treat and/or prevent injuries; (ii) corrective exercises; (iii) performance training exercises; and (iv) protocols to maximize physical performance; and
f. data points being derived from said athletic assessment and said one or more analytical algorithm and said one or more data mining algorithms comparing said data points against other aspects of athleticism, including kinematics, joint kinematics, muscle activation, acceleration, power output, fatigue index, force production, total body control (both gross and fine motor) power, explosiveness, static weight distribution, and cognitive and sensory response.

2. The system as in claim 1, wherein said athletic protocol is sport specific.

3. The system of claim 2, wherein said athletic protocol is position specific.

4. The system of claim 1, wherein said athletic assessment comprises 3D biomechanics, kinematics of running and jumping mechanics.

5. The system of claim 1, wherein said athletic assessment comprises lower and upper extremity capacity.

6. The system of claim 1, wherein said athletic assessment comprises agility, balance and explosiveness.

7. The system of claim 1, wherein said athletic assessment comprises measuring and recording reaction time.

8. The system of claim 1, wherein said athletic assessment further comprises: movement efficiency; rotational inertia+momentum; increase core strength+center of gravity; hip mobility+stability; upper+lower body muscle strength; endurance+stamina; and sensory+motor skills.

9. The system of claim 1, wherein said athletic assessment further comprises: muscular adhesions; range of motion; soreness+inflammation; flexibility; and lymphatic drainage.

10. A method for collecting and analyzing physical performance of an individual for structuring and generating an athletic protocol, the steps comprising:
a. performing an athletic assessment comprising measuring kinetic, neurological, musculoskeletal and aerobic capacity of said individual and recording athletic data;
b. using a computer system comprising a display, digital data storage medium and a central processing unit (CPU) operable with programming to collect, store and analyze said athletic data;
c. using one or more analytical algorithm to assess injury risk levels of said individual based on said athletic data;
d. performing one or more data mining algorithm using artificial intelligence to improve the method's predictive modeling and analytics;
e. using said one or more analytical algorithm and said one or more data mining algorithm to compare data points derived from said athletic assessment against other aspects of athleticism, including kinematics, joint kinematics, muscle activation, acceleration, power output, fatigue index, force production, total body control (both gross and fine motor) power, explosiveness, static weight distribution, and cognitive and sensory response; and
f. structuring and analyzing said athletic data to generate said athletic protocol for said individual comprising: (i) information to correct imbalances to treat and/or prevent injuries; (ii) corrective exercises; (iii) performance training exercises; and (iv) protocols to maximize physical performance.

11. The method of claim 10, wherein said athletic protocol is sport specific.

12. The method of claim 11, wherein said athletic protocol is position specific.

13. The method of claim 10, wherein said athletic assessment comprises measuring and recording 3D biomechanics, kinematics of running and jumping mechanics.

14. The method of claim 10, wherein said athletic assessment comprises measuring and recording lower and upper extremity capacity.

15. The method of claim 10, wherein said athletic assessment comprises measuring and recording agility, balance and explosiveness.

16. The method of claim 10, wherein said athletic assessment comprises measuring and recording reaction time.

17. The method of claim 10, wherein said athletic assessment further comprises: movement efficiency; rotational inertia+momentum; increase core strength+center of gravity; hip mobility+stability; upper+lower body muscle strength; endurance+stamina; and sensory+motor skills.

18. The method of claim 10, wherein said athletic assessment further comprises: muscular adhesions; range of motion; soreness+inflammation; flexibility; and lymphatic drainage.

19. A non-transitory computer storage readable medium for collecting and analyzing physical performance of an individual to structure and generate an athletic protocol, comprising computer-useable instructions that, when used by one or more computing devices, cause the one or more computing devices to:
a. generate and receive data from an athletic assessment comprising measuring kinetic, neurological, musculoskeletal and aerobic capacity of said individual and recording athletic data;
b. collect, store and analyze said athletic data;
c. assess injury risk levels of said individual based on said athletic data using one or more analytical algorithm;
d. perform one or more data mining algorithm using artificial intelligence for predictive modeling and analytics;
e. compare, using said one or more analytical algorithm and said one or more data mining algorithm, data points derived from said athletic assessment against other aspects of athleticism, including kinematics, joint kinematics, muscle activation, acceleration, power output, fatigue index, force production, total body control (both gross and fine motor) power, explosiveness, static weight distribution, and cognitive and sensory response; and
f. structure and analyze said athletic data to generate said athletic protocol for said individual comprising: (i) information to correct imbalances to treat and/or prevent injuries; (ii) corrective exercises; (iii) performance training exercises; and (iv) protocols to maximize physical performance.

* * * * *